(12) United States Patent
Yagi (10) Patent No.: US 6,982,027 B2
(45) Date of Patent: Jan. 3, 2006

(54) BIOSENSOR

(75) Inventor: Yuji Yagi, Kyoto (JP)

(73) Assignee: Arkray, Inc., Kyoto (JP)

( * ) Notice: Subject to any disclaimer, the term of this patent is extended or adjusted under 35 U.S.C. 154(b) by 76 days.

(21) Appl. No.: 10/399,874

(22) PCT Filed: Oct. 25, 2001

(86) PCT No.: PCT/JP01/09367

§ 371 (c)(1),
(2), (4) Date: Apr. 22, 2003

(87) PCT Pub. No.: WO02/35222

PCT Pub. Date: May 2, 2002

(65) Prior Publication Data

US 2004/0040839 A1   Mar. 4, 2004

(30) Foreign Application Priority Data

Oct. 27, 2000  (JP)  ............................ 2000-328130

(51) Int. Cl.
*G01N 27/327*  (2006.01)
(52) U.S. Cl. .............................. 204/403.06; 204/403.05
(58) Field of Classification Search .............................. 204/403.01–403.14, 416–418
See application file for complete search history.

(56) References Cited

U.S. PATENT DOCUMENTS

| | | | |
|---|---|---|---|
| 4,605,621 A * | 8/1986 | Pinnavaia et al. .......... | 435/177 |
| 5,205,920 A | 4/1993 | Oyama et al. ......... | 204/403.11 |
| 5,494,562 A | 2/1996 | Maley et al. ................ | 257/414 |
| 5,696,314 A | 12/1997 | McCaffrey et al. ......... | 205/778 |
| 6,077,408 A | 6/2000 | Miyamoto et al. ....... | 204/403.1 |
| 6,627,057 B1 * | 9/2003 | Bhullar et al. ......... | 204/403.01 |

FOREIGN PATENT DOCUMENTS

| | | | |
|---|---|---|---|
| EP | 0690134 A1 * | 3/1996 | |
| EP | 0 856 586 | 8/1998 | |
| EP | 0 909 952 | 4/1999 | |
| JP | 63-58149 | 3/1988 | |
| JP | 03160358 A * | 7/1991 | |
| JP | 03170854 A * | 7/1991 | |
| JP | 3-202764 | 9/1991 | |
| JP | 5-133929 | 5/1993 | |
| JP | 6-54304 | 7/1994 | |
| JP | 6-213858 | 8/1994 | |
| JP | 2517153 | 4/1996 | |
| JP | 8-193969 | 7/1996 | |
| JP | 8-94574 | 12/1996 | |
| JP | 9-318588 | 12/1997 | |

(Continued)

OTHER PUBLICATIONS

JPO computer translation of Satoshi et al. (JP 2000-081407 A).*

(Continued)

*Primary Examiner*—Alex Noguerola
(74) *Attorney, Agent, or Firm*—Hamre, Schumann, Mueller & Larson, P.C.

(57) ABSTRACT

A biosensor is provided, which can measure an analyte in a sample with high precision. The biosensor is produced by disposing a electrode system including a working electrode 12 and a counter electrode 13 on a substrate 11, and then forming a reagent layer 16 containing a reagent and particulates on the electrode system. The influence of the impurities in the sample on the electrode system can be eliminated by the particulates. The average particle diameter of the particulates preferably is in the range from 0.1 to 45 $\mu$m.

19 Claims, 4 Drawing Sheets

FOREIGN PATENT DOCUMENTS

| | | |
|---|---|---|
| JP | 10-221293 | 8/1998 |
| JP | 2000-81407 | 3/2000 |
| JP | 2000-221157 A | 8/2000 |

OTHER PUBLICATIONS

JPO computer translation of Yoshiko et al. (JP 08-094574 A).*

JPO abstract for Koichi (JP 03170854 A).*

JPO abstract for Koichi (JP 03160358 A).*

CAPLUS abstract of Lei et al. ( Studies on employing tetrathiafulvalene as an electron shuttle incorporated in a montmorillonite modified immobilization matrix for an enzyme electrode, Journal of Electroanalytical Chemistry (1996), 419(1), 93-98).*

CAPLUS abstract of Shyu et al. ("Characterizations of iron-containing clay modified electrodes and their applicaitosn for glucos sensing," Journal of the Electrochemical Society (1998), 145(1), 154-158).*

Zen et al. ("An Enzymatic Clay-Modified Electrode for Aerobic Glucose Monitoring with Dopamine as Mediator," Anal. Chem. 1997, 69, 1669-1673).*

Blood article from the Grolier Multimedia Encyclopedia 2004.*

Anthony Turner ("Redox Mediators and their Application in Amperometric Sensors," Analytical Uses of Immobilized Biologica Compounds for Detection, Medical and Industrial Uses, 131-140, Guilbault and Mascini (eds.), 1988, Reidel Publishing Company.*

Jyh-Myng Zen et al., "A Glucose Sensor Made of an Enzymatic Clay-Modified Electrode and Methyl Viologen Mediator", Analytical Chemistry, vol. 68, No. 15, Aug. 1, 1996, pp. 2635-2640.

Takeo Ohsaka et al., "A New Amperometric Glucose Sensor Based on Bilayer Film Coating of Redox-Active Clay Film and Glucose Oxidase Enzyme Film", Bulletin of the Chemical Society of Japan, vol. 63, No. 9, 1990, pp. 2646-2652, The Chemical Society of Japan. month of pubn not known.

* cited by examiner

BIOSENSOR

CROSS REFERENCE TO RELATED APPLICATIONS

This application is a 35 U.S.C. 371 of PCT application PCT/JP01/09367 filed on Oct. 25, 2001.

TECHNICAL FIELD

The present invention relates to a biosensor.

BACKGROUND ART

Biosensors that can quantify a specific analyte in a sample simply and rapidly, for example, without dilution or stirring of the sample have been used widely. In general, such a biosensor can be produced by forming an electrode system having a working electrode (also referred to as "measuring electrode") and a counter electrode on an electrically insulating substrate by a method such as screen printing, and then forming a reactive layer including a redox enzyme that reacts with the analyte and an electron-accepting substance on the electrode system, as disclosed in Japanese Patent No. 2517153, for example. When the reactive layer is in contact with the sample containing the analyte, the analyte is oxidized by the catalytic action of the redox enzyme, and the electron-accepting substance is reduced at the same time. The reduced electron-accepting substance is re-oxidized by an electrochemical approach, and the concentration of the analyte in the sample can be calculated from the thus obtained oxidation current values.

However, such a biosensor has a problem in that there may be errors in the measurement, depending on the properties or the like of the sample. For example, in the case where a whole blood is used as a sample, solid components such as blood cells and soluble/insoluble components such as lipid, protein, and saccharides are adsorbed on the surface of the electrodes, thereby making an accurate measurement difficult. Furthermore, there is a large difference between individuals in the hematocrit (Hct) value, which is a volume ratio of erythrocytes to whole blood, so that there is a difference between specimens in the above-described influence on the biosensor. Such an influence due to the above-described impurities can be decreased by, for example, diluting the sample and then subjecting the diluted sample to a biosensor. However, this takes more time and complicates the operation.

In order to avoid the influence due to the impurities, the following methods have been proposed, for example: forming a water absorptive polymer layer on electrodes (JP 6(1994)-54304 B); forming a layer containing a water insoluble polymer and a water-soluble polymer on a reactive layer (JP 6(1994)-213858 A); forming a polymer film made of a mixture of a lipid-soluble polymer and an amphiphile polymer on electrodes (JP 9(1997)-318588 A); forming an anion filter for suppressing the solid components from passing therethrough on a reactive layer (JP 10(1998)-221293 A); and fixing a microcapsule containing a sodium citrate solution onto an electrode on which glucose oxidase is immobilized, and using the electrode as a working electrode (JP 5(1993) 133929 A).

DISCLOSURE OF INVENTION

However, the method employing the anion filter has a problem in that, although the anion filter is effective in suppressing the solid components from passing therethrough, it has no effect on the soluble components, such as protein, in the sample, for example. Furthermore, in the methods other than this method, since the water-soluble polymer and the like are used, the water absorptivity is high so that the biosensor is susceptible to humidity, which causes a problem in that the enzyme reaction is slow, for example.

Therefore, it is an object of the present invention to provide a biosensor that can measure an analyte in a sample with high precision without being affected by impurities in the sample or humidity.

In order to solve the above-described problems, a biosensor of the present invention includes a substrate, a reagent layer containing a reagent, and an electrode system including a working electrode and a counter electrode, the electrode system being disposed on the substrate, and the reagent layer being formed on the electrode system, wherein the reagent layer further includes particulates.

In the biosensor of the present invention, impurities in the sample can be prevented from becoming attached to the electrode surface by letting the reagent layer contain the particulates. Furthermore, the biosensor is not susceptible to the influence of humidity because it is not necessary to use the above-described water-soluble polymer and the like. Therefore, the sensitivity of the biosensor is prevented from deteriorating, regardless of the properties of the sample, and an analyte can be measured with high precision. The reason why the particulates can prevent the impurities from becoming attached to the electrode surface is still unknown. However, it is considered that this is caused by the physical adsorption or the like of the impurities to the particulates.

In the biosensor of the present invention, the reagent layer may be a single layer or a laminate including a reagent-containing layer containing the reagent and a particulate-containing layer containing the particulates.

In the case where the reagent layer is the laminate, the reagent-containing layer may be formed on the electrodes via the particulate-containing layer. However, it is preferable that the particulate-containing layer is formed on the electrodes via the reagent-containing layer, because, for example, the adsorption of the impurities onto the electrodes can further be eliminated, and the analyte in the sample and the reagent can react with each other easily.

The average particle diameter of the particulates is, for example, in the range from 0.1 to 45 µm, preferably 0.5 to 30 µm, more preferably 1 to 20 µm, and particularly preferably 3 to 15 µm. If the average particle diameter is 0.1 µm or more, it is easy for a sample to permeate the reagent layer sufficiently and the sensitivity of the biosensor can be improved. If the average particle diameter is 45 µm or less, the influence of the impurities in the sample can be eliminated sufficiently.

The average particle diameter can be obtained by, for example, observing directly the particulates through an electron microscope and measuring the particle diameter to calculate the average. There is no limitation regarding the number of the particulates to be measured. For example, the number of the particulates to be measured can be 100 or more, and preferably in the range from 100 to 300.

There is no limitation regarding the particle size distribution of the particulates, but preferably, it is in the range from 0.01 to 100 µm, more preferably 0.05 to 60 µm, and particularly preferably 0.1 to 40 µm.

As the particulates, spherical or spheroidal particulates, or a spherical aggregate of particulates can be used, for example. However, spherical particulates are preferable because the layer containing the particulates can be uniform and retain an appropriate density.

The particulates preferably are formed of a polymer compound, and more preferably are formed of a polymer compound that does not contain an impurity causing electrolysis and is electrochemically inactive. Furthermore, it is preferable that the polymer compound is water insoluble. Specific examples of the polymer compound includes a polymer or a copolymer containing at least one of acrylic acid, methacrylate, maleate, acrylic ester, methacrylic acid ester, maleate ester, and a styrene derivative monomer. Examples of the styrene derivative polymer include styrene and alkylstyrene. In addition, urethane compounds such as polyurethane and polyurea; polyolefin polymer compounds such as polyethylene and polypropylene; polyolefin derivatives such as polyvinyl chloride; and polyamide compounds can be used, for example. In addition to the polymer compounds, the particulates may be formed of inorganic compounds such as ceramics typified by silica gel, alumina, zeolite, apatite, glass, and alite, for example. Among these, a polymer or a copolymer containing at least one of acrylic acid, methacrylate, maleate, acrylic ester, methacrylic acid ester, maleate ester, and a styrene derivative monomer, and a polyamide-based polymer compound are preferable, because they are electrochemically inactive. More specifically, polymethacrylate (PMMA), polystyrene (PS), polyamide (PA) and the like are particularly preferable.

Examples of suitable particulates include a commercially available product named Techpolymer bmx-5 (SEKISUI PLASTICS Co., Ltd., PMMA, spherical, a particle diameter 5 $\mu$m), a product named Ganzpearl GM-0600 (GANZ CHEMICAL CO., LTD., PMMA, spherical, a particle diameter 6 $\mu$m), a product named Ganzpearl GS-0805 (Ganz Kasei Co. Ltd., crosslinked PS, spherical, a particle diameter 8 $\mu$m), a product named Ganzpearl PS-8F (Ganz Kasei Co. Ltd., PMMA, spherical, a particle diameter 0.4 $\mu$m), a product named Orgasol 2002 EXD NAT COS Type S (Elf Atochem, nylon, spheroidal, a size 10 $\mu$m), a product named Trefil E-506C (Dow Corning Toray Silicone Co., Ltd., crosslinked silicone, spherical, a particle diameter 10 $\mu$m), a product named Saramics SN-E-02 (UBE INDUSTRIES, LTD., silicon nitride, spherical, a particle diameter 1 $\mu$m), a product named Gotball (SUZUKI OIL & FATS CO., LTD., silica, spherical, a particle diameter 10 $\mu$m), a product named Glassbeads (Polysciences, Inc., lime glass, spherical, a particle diameter 3 to 10 $\mu$m), and the like.

Furthermore, it is preferable that the particulates are electrically inactive. Also, it is preferable to change the particle diameter in accordance with the impurities to be removed, and to change the characteristics of the surface of the particulates. For example, when it is desired that the surface of the particulates is hydrophobic, it is preferable to use particulates formed of PS. When it is desired that the surface of the particulates is more hydrophilic than PS, it is preferable to use particulates formed of PMMA, PA, or the like. Furthermore, when it is desired that the surface of the particulates is negatively charged, it is preferable to use particulates formed of PS or the like to which a carboxyl group is introduced. When it is desired that the surface of the particulates is positively charged, it is preferable to use particulates formed of PS or the like to which an amino group is introduced.

More specifically, in the case where blood cells in whole blood are to be removed, particulates having a diameter of not more than about 7 $\mu$m preferably are used, for example. Because the erythrocytes constituting a large proportion of the whole blood have an average diameter of about 7 $\mu$m, the erythrocytes can be separated efficiently by using such particulates. On the other hand, in the case where a plurality of proteins in whole blood are to be removed, any number of proteins can be removed through adsorption, for example, by using particulates formed of a mixture obtained by mixing PS, PS to which a carboxyl group is introduced, PS to which an amino group is introduced, and the like as appropriate. It is to be noted here that methods of removing these components are not limited to the above-described methods.

In the biosensor of the present invention, it is preferable that the reagent layer further contains an inorganic gel. When the reagent layer contains an inorganic gel, the adsorption of the impurities onto the electrodes can further be prevented, and the diffusion of the sample also can be prevented. As a result, the enzyme reaction occurs in a narrow region so that the reagent and the analyte can react with each other rapidly.

An inorganic gel-containing layer containing an inorganic gel may be formed between the electrode system and the reagent layer separately, for the same reason as described above.

It is preferable that the inorganic gel is a gel of clay mineral. Examples of the inorganic gel include expansive phyllosilicate. As the expansive phyllosilicate, smectite, expansive mica, and the like are preferable, for example. Preferable examples of the smectite include hectorite, saponite, and montmorillonite, and preferable examples of the expansive mica include sodium tetrasilicon fluoride mica and teniorite. These inorganic gels can be used alone or in combination with two or more types.

As the smectite, a product named Labonight XLG and a product named Labonight XLS (both manufactured by Laboat Industries Co. Ltd.), a product named Lucentite SWN and a product named Lucentite SWF (CO-OP CHEMICAL Co. Ltd.), and a product named Chikisopi W (Kyowa Chemical Industry Co., Ltd.), which are commercially available synthesized hectorite; a product named Smecton SA (Kunimine Industries, Co. Ltd.), which is a commercially available synthesized saponite; a product named Kunipia F (Kunimine Industries, Co. Ltd.), which is a commercially available natural montmorillonite purified product; or the like can be used, for example.

Further, as the expansive mica, a product named Na-TS (TOPY INDUSTRIES LIMITED), which is a commercially available sodium tetrasilicon fluoride mica, a product named Li-TN (TOPY INDUSTRIES LIMITED), which is a commercially available teniorite, or the like can be used, for example.

In the biosensor of the present invention, it is preferable that a surfactant-containing layer containing a surfactant further is formed on the reagent layer. If the surfactant-containing layer is provided in this manner, a hydrophilic film is formed on the surface of the reagent layer, so that the sample and the reagent can be mixed quickly and uniformly. Consequently, a reaction proceeds rapidly, and the repeatability can be improved.

In the case where the above-described reagent layer is the laminate, it is preferable that the surfactant-containing layer containing a surfactant is formed on the particulate-containing layer.

Examples of the surfactant include cationic surfactants, anionic surfactants, ampholytic surfactants, nonionic surfactants, and natural surfactants. Among these, cationic surfactants, nonionic surfactants, and natural surfactants are preferable, and nonionic surfactants and natural surfactants are more preferable. As the natural surfactants, phospholipid can be used, for example, and lecithin such as egg yolk lecithin, soybean lecithin, hydrogenated lecithin, and high purity lecithin can be used preferably. As the nonionic surfactants, polyoxyethylene sorbitan fatty acid esters such as a product named Tween 20, polyoxyethylene alkyl ether such as a product named Triron X-100, polyoxyethylene phenyl alkyl ether such as a product named Triton X-405, or the like can be used, for example. Among these, phospholipid is particularly preferable, and lecithin such as high purity lecithin is most preferable.

In the biosensor of the present invention, for the electrodes, any electrodes can be used, as long as they can detect electrochemically a reaction between the analyte and the reagent. For example, gold electrodes, carbon electrodes, silver electrodes, or the like can be used. Among these, because of excellent electrical conductivity and chemical stability, gold electrodes and carbon electrodes are preferable, and carbon electrodes are more preferable.

In the biosensor of the present invention, there is no particular limitation regarding the reagent, as long as it can react with the analyte and the reaction can be electrochemically detected. However, it is preferable that, for example, the reagent contains an enzyme. Examples of the enzyme include redox enzymes.

The redox enzyme can be determined as appropriate, depending on the type of the analyte. More specifically, glucose oxidase, glucose dehydrogenase, lactate oxidase, lactate dehydrogenase, fructose dehydrogenase, galactose oxidase, cholesterol oxidase, cholesterol dehydrogenase, alcohol oxidase, alcohol dehydrogenase, bilirubinate oxidase, glucose-6-phosphate dehydrogenase, amino-acid dehydrogenase, formate dehydrogenase, glycerol dehydrogenase, acyl-CoA oxidase, choline oxidase, 4-hydroxybenzoic acid hydroxylase, maleate dehydrogenase, sarcosine oxidase, uricase, and the like can be used, for example.

Further, when the enzyme is a redox enzyme, it is preferable that the reagent contains an electron acceptor in a reaction of the enzyme.

As the electron acceptor, potassium ferricyanide, p-benzoquinone, phenazine methosulfate, indophenol and derivatives thereof, β-naphthoquinone-4-sulfonic acid potassium salt, methylene blue, ferrocene and derivatives thereof, osmium complexes, ruthenium complexes, $NAD^+$, $NADP^+$, pyrrolo-quinoline quinine (PQQ), and the like can be used, for example. Among these, potassium ferricyanide, ferrocene, osmium complexes, $NAD^+$, $NADP^+$, and the like are preferable.

In the biosensor of the present invention, there is no limitation regarding the sample to be measured, but the present invention is useful for, for example, samples containing the impurities such as soluble components, insoluble components, solid components, and the like. Examples of the impurities include proteins, lipids, saccharides, and blood cells. Specific examples of the sample to be measured include biological samples such as whole blood, blood plasma, blood serum, sputum, urine, and liquor cerebrospinalis, drinks such as juice, foods such as soy sauce and sauce, waste water, rainwater, water for a swimming pool and the like. Among these, whole blood, blood plasma, blood serum, sputum, liquor cerebrospinalis, and the like are preferable, and whole blood is more preferable.

BRIEF DESCRIPTION OF DRAWINGS

FIGS. 1A to 1C show an example of a biosensor of the present invention.

FIGS. 2A to 2C show another example of a biosensor of the present invention.

BEST MODE FOR CARRYING OUT THE INVENTION

Hereinafter, embodiments of the present invention will be described more specifically.

(Embodiment 1)

Figure 1:
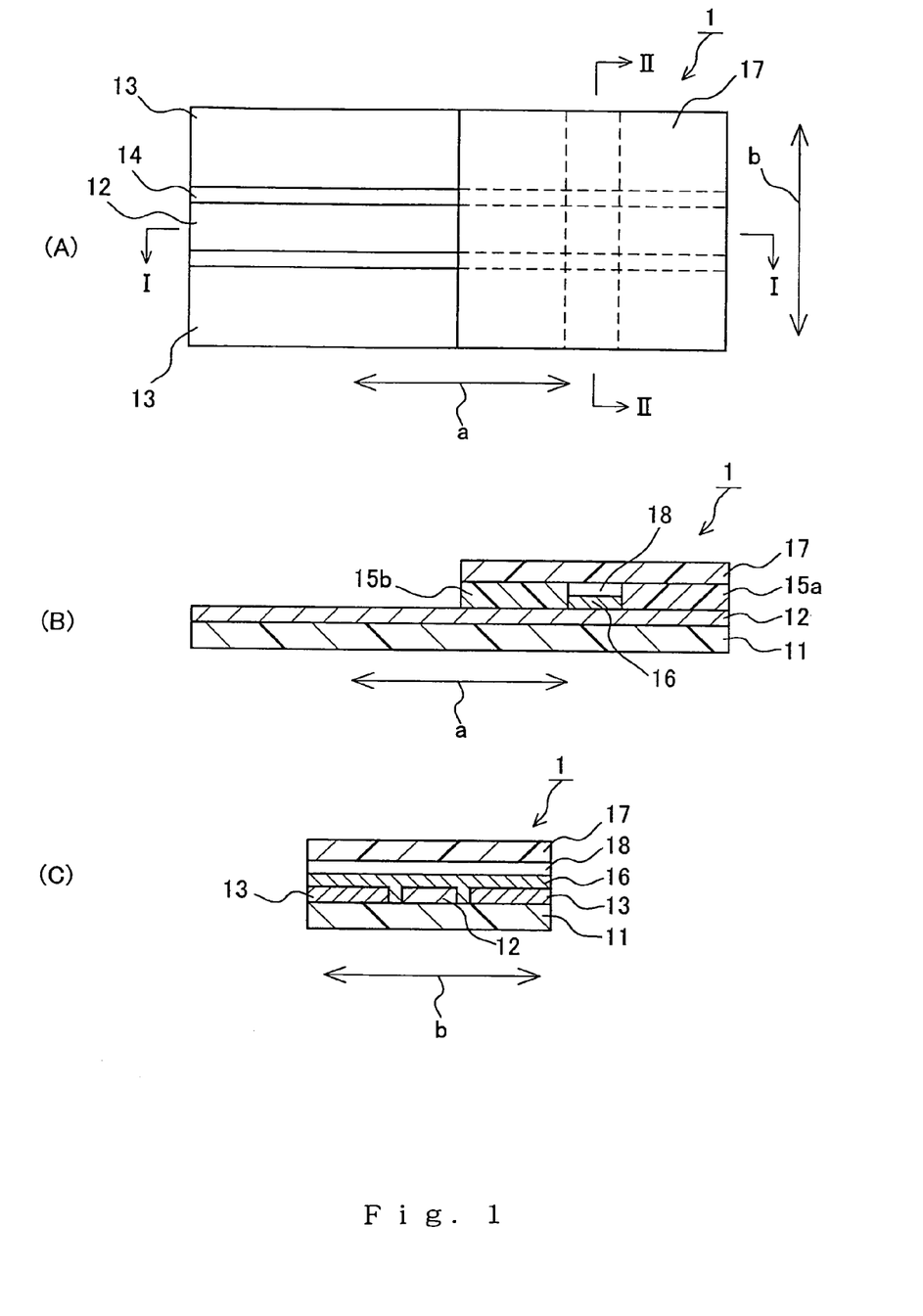
FIG. 1A is a plan view of the biosensor.
FIGS. 1B and 1C are cross-sectional views of the same.

FIGS. 1A–1C show an example of a biosensor of the present invention. FIG. 1A is a plan view of the biosensor, FIG. 1B is a cross-sectional view taken along the line I—I of FIG. 1A, and FIG. 1C is a cross-sectional view taken along the line II—II of FIG. 1A. As shown in the drawings, in this biosensor 1, an electrode system including a working electrode 12 and counter electrodes 13 is disposed on a substrate 11. A reagent layer 16, which is a single layer containing a reagent and particulates, is formed on one end portion (on the right side of FIG. 1A, and at the upper right of FIG. 1B) of the electrode system. The two counter electrodes 13 are disposed on the opposite ends in the width direction (the direction indicated by the arrow "b") of the substrate 11, and the working electrode 12 is disposed in the center in the width direction of the substrate 11. These electrodes 12 and 13 extend in the longitudinal direction (the direction indicated by the arrow "a") of the substrate 11. An insulating portion 14 is formed between the working electrode 12 and each of the counter electrodes 13. On the end portion of the electrode system, spacers 15a and 15b are disposed so as to be perpendicular to the electrode system, and the reagent layer 16 is disposed between the spacers 15a and 15b. A cover 17 is disposed on the spacers 15a and 15b so as to cover the upper portion of the reagent layer 16, thereby forming a hole passing through the biosensor in the width direction between the cover 17 and the reagent layer 16. This hole serves as a sample supply hole 18.

The size of the biosensor 1 is not limited to a particular value, and can be set as appropriate, depending on the amount of a sample to be supplied or the like. For example, the size of the biosensor 1 is 10 to 50 mm for the total length, 2 to 20 mm for the total width, 500 to 1500 μm for the maximum thickness, and 300 to 500 μm for the minimum thickness, and preferably, 10 to 30 mm for the total length, 2 to 10 mm for the total width, 500 to 1000 μm for the maximum thickness, and 300 to 400 μm for the minimum thickness.

The size of the reagent layer 16 is, for example, 0.2 to 10 mm for the length, 2 to 20 mm for the width, and 5 to 400 μm for the thickness, and preferably, 0.2 to 5 mm for the length, 2 to 10 mm for the width, and 10 to 200 μm for the thickness. The size of the substrate 11 is, for example, 10 to 50 mm for the length, 2 to 20 mm for the width, and 50 to 1000 μm for the thickness, and preferably, 10 to 30 mm for the length, 2 to 10 mm for the width, and 50 to 500 μm for the thickness. The size of the spacers 15a and 15b is, for example, 1 to 20 mm for the length, 2 to 20 mm for the width, and 10 to 500 μm for the thickness, and preferably, 2 to 10 mm for the length, 2 to 10 mm for the width, and 20 to 300 μm for the thickness. The size of the cover 17 is, for example, 10 to 50 mm for the length, 2 to 20 mm for the width, and 50 to 1000 µm for the thickness, and preferably, 10 to 30 mm for the length, 2 to 10 mm for the width, and 50 to 500 µm for the thickness. The size of the hole 18 is, for example, 0.2 to 10 mm for the length, 0.2 to 20 mm for the width, and 5 to 500 µm for the height, and preferably, 0.2 to 5 mm for the length, 2 to 10 mm for the width, and 10 to 300 µm for the height. It should be noted that "length" of each portion refers to the length in the longitudinal direction of the biosensor, and "width" refers to the length in the width direction of the same.

More specifically, in the case where about 2 µL of a sample is to be supplied, the size of the reagent layer 16 is, for example, 0.2 to 2 mm for the length, 2 to 20 mm for the width, and 5 to 400 µm for the thickness, and preferably, 0.4 to 1 mm for the length, and 2 to 10 mm for the width, 10 to 200 µm for the thickness. Further, the size of the hole 18 is, for example, 0.2 to 2 mm for the length, 2 to 20 mm for the width, and 50 to 500 µm for the height, and preferably, 0.4 to 1 mm for the length, 2 to 10 mm for the width, and 100 to 300 µm for the height.

The content of the particulates in the reagent layer 16 can be determined as appropriate, depending on the type or the amount of a sample to be supplied or the like. For example, the content of the particulates for about 2 µL of the sample can be in a range from 0.01 to 1 mg, and more preferably 0.05 to 0.5 mg.

The content of the reagent in the reagent layer 16 is not limited to a particular value, and can be determined as appropriate, depending on the type of the reagent, the type or the amount of the sample to be supplied, or the like. For example, when an enzyme is used as the reagent, the content of the enzyme for about 2 µL of the sample preferably is in the range from 0.05 to 50 U, and more preferably 0.1 to 20 U. Further, when an electron acceptor is used, the content of the electron acceptor for about 2 µL of the sample preferably is in the range from 0.01 to 100 µmol, and more preferably 0.05 to 50 µmol. More specifically, when GOD is used as an enzyme and potassium ferricyanide is used as an electron acceptor, the content of GOD for about 2 µL of the sample preferably is in the range from 0.1 to 20 U, and more preferably 0.2 to 10 U, and the content of potassium ferricyanide for about 2 µL of the sample preferably is in the range from 0.05 to 50 µmol, and more preferably 0.1 to 10 µmol.

Such a biosensor can be produced, for example, in the following manner. First, the substrate 11 on which the electrodes and the like are to be formed is prepared. The substrate 11 preferably is formed of an electrically insulating material, such as plastics, glass, paper, and ceramics. Examples of the plastics include polyethylene terephthalate (PET), PS, PMMA, and polypropylene (PP).

Next, the electrode system including the working electrode 12 and the counter electrodes 13 is formed on the substrate 11. As the electrodes, gold electrodes, carbon electrodes, or the like are preferable as described above, and the electrodes can be formed by a known method, in accordance with the type of the electrodes.

The gold electrodes can be formed by, for example, an evaporation method, plating, a gold foil attachment method, or the like. The evaporation method can be ion plating performed for 2 minutes at a vacuum degree of $1.33 \times 10^{-4}$ Pa, an input power of 300 W, and a rate of 5 Å/sec. Such ion plating is performed in the following manner, for example. First, gold is deposited on a plastic sheet such as PET, and a slit is formed on the gold foil layer deposited on the sheet using a kisscut device. The slit serves as an insulating portion, thereby forming a working electrode and a counter electrode.

Alternatively, carbon electrodes can be formed by, for example, means for screen-printing, coating, or plating carbon ink on the substrate 11.

It is preferable that the surfaces of the electrodes are treated so as to be hydrophilic before the reagent layer 16 as described later is formed on the electrodes. Thus, the surfaces of the electrodes that are hydrophobic are made hydrophilic by the above-described treatment, which facilitates uniform formation of the reagent layer in the case where the reagent layer is formed using a reagent solution as described later.

The method for the treatment for hydrophilicity can be determined as appropriate, depending on the type of the electrodes. When the electrodes are gold electrodes, for example, the treatment for hydrophilicity can be performed by immersing the electrodes in a hydrophilic solution such as a mercaptoethanol solution and a mercaptoethanol amine solution, and then washing and drying them.

As a solvent for the hydrophilic solution, for example, organic solvents such as ethanol, butanol, acetone, and tetrahydrofuran can be used. The concentration of the hydrophilic solution is, for example, in the range from 0.01 to 100 mmol/L, preferably 0.05 to 50 mmol/L. For washing, organic solvents, such as ethanol, methanol, butanol, acetone, and tetrahydrofuran, or washing solutions such as purified water can be used, for example.

In the case where the electrodes are carbon electrodes, the treatment for hydrophilicity can be performed by, for example, immersing the electrodes in a surfactant and then washing them with purified water.

Next, the spacers 15a and 15b are disposed on the substrate 11 on which the electrode system has been formed. As shown in the drawings, by arranging these two spacers 15a and 15b so as to be parallel to the width direction and apart from each other at a certain distance, a space for forming the reagent layer 16 as described later can be secured. The spacers 15a and 15b can be made of, for example, a resin film or tape. If it is a double-faced tape, the cover as described later can be attached easily. In addition to that, the spacers can be formed by resist printing or other means, for example.

Next, the reagent layer 16, which is a single layer containing a reagent and particulates, is formed in the space between the spacers 15a and 15b.

As the reagent and the particulates, those described above can be used. The reagent layer can be formed by preparing a solution containing the particulates and the various reagents and then pouring the solution into the space between the spacers 15a and 15b.

The solution can be prepared, for example, by dissolving the reagent in a solvent sufficiently and then dispersing the particulates in the solvent. There is no particular limitation regarding the solvent. For example, water, buffers, or organic solvents such as ethanol, methanol, butanol, dimethylsulfoxide (DMSO), and tetrahydrofuran can be used. Examples of the buffer include phosphate buffer, citrate buffer, acetate buffer, Tris-HCl buffer, and Good's buffer. The pH thereof preferably is in the range from 4 to 9, more preferably 5 to 8. Examples of the water include purified water, distilled water, and ultrapure water. Among these, ultrapure water is preferable, because a biosensor that hardly contains impurities and has a high precision can be produced.

There is no limitation regarding the concentration of the particulates in the solution, but preferably, it is in the range from 10 to 1000 g/L, more preferably 50 to 500 g/L.

There is no limitation regarding the concentration of the reagent in the solution. For example, in the case of an enzyme, the concentration preferably is in the range from 10 to 10,000 KU/L, more preferably 50 to 5000 KU/L. In the case where an electron acceptor is contained, the concentration preferably is in the range from 0.01 to 10 mol/L, more preferably 0.05 to 5 mol/L.

After the solution has been prepared, the solution is poured into the space between the spacers 15a and 15b. There is no limitation regarding the method for pouring the solution. For example, the solution can be poured with an automatically driven dispenser or the like. In order to prevent the particulates from settling, it is preferable to pour the solution while stirring the solution.

The amount of the solution to be poured can be determined as appropriate, depending on the size of the reagent layer to be formed, the content of the reagent and the particulates, or the like. However, it is preferable that 0.1 to 10 $\mu$L of the solution is poured per 10 $mm^2$ of the reagent layer to be formed, more preferably 0.2 to 5 $\mu$L.

After the solution has been poured, the solution is dried to form the reagent layer. There is no limitation regarding the means for drying the poured solution. For example, natural curing, air drying, drying under reduced pressure, lyophilization under reduced pressure, or the like can be used. These methods can be used in combination.

In the case of hot air drying, the conditions are as follows, for example: the temperature in the range from 10 to 60° C., the relative humidity in the range from RH 5 to 40%, and the time in the range from 1 to 30 minutes.

Next, the cover 17 is disposed on the spacers 16a and 15b so as to cover the reagent layer 16. Thus, a hole is formed between the reagent layer 16 and the cover 17, and this hole serves as a sample supply hole 18.

There is no limitation regarding the material of the cover 17. For example, various plastics can be used.

It is preferable that the thus produced biosensor 1 is stored air-tightly together with a desiccant such as molecular sieves, silica gel, and calcium oxide in order not to be affected by humidity, when it is stored for a long time. The biosensor 1 can be used in combination with measuring equipment provided with, for example, means for applying a predetermined voltage for a certain time, means for measuring an electrical signal transmitted from the biosensor, means for calculating the electrical signal into the concentration of the analyte, and other means.

The use of the biosensor 1 will be described by taking an example in which a sample is whole blood, the analyte is glucose, and the reagents are GOD and potassium ferricyanide.

First, the whole blood sample is drawn in the biosensor 1 from the hole 18 by the capillary phenomenon or the like. Impurities such as blood cells in the whole blood can be prevented from becoming attached to the electrodes by the particulates present in the reagent layer 16. On the other hand, the glucose in the sample is oxidized by the GOD, and the potassium ferricyanide is reduced by electrons that have been moved by the oxidation reaction, so that potassium ferrocyanide is produced. Then, after a predetermined time has passed since the supply of the whole blood sample, a voltage is applied between the counter electrodes 13 and the working electrode 12 by the above-described means for applying the voltage, so that the reduced potassium ferrocyanide is reoxidized electrochemically into potassium ferricyanide, and the oxidation current at that time is detected by the above-described means for measuring the electrical signal. The peak value of the oxidation current is proportional to the glucose concentration in the sample, so that the glucose concentration in the sample can be obtained by converting this value to the glucose concentration by the calculating means. According to such a biosensor, the impurities in the sample cannot be adsorbed in the electrodes, as described above, so that the sensitivity is prevented from being deteriorated, and measurement can be performed with high precision. In addition, the biosensor is not susceptible to the influence of humidity.

In this biosensor 1, for example, the reagent layer may further contain an inorganic gel. As the inorganic gel, those described above can be used. The content of the inorganic gel in the reagent layer can be determined as appropriate, depending on the type thereof, the type or the amount of the sample, or the like. For example, the content of the inorganic gel for about 2 $\mu$L of a sample can be in a range from 0.1 to 100 $\mu$g, and more preferably 0.5 to 50 $\mu$g. A reagent layer containing such an inorganic gel can be formed by preparing a solution containing the reagent, particulates, and inorganic gel in the same manner as described above.

(Embodiment 2)

Figure 2:
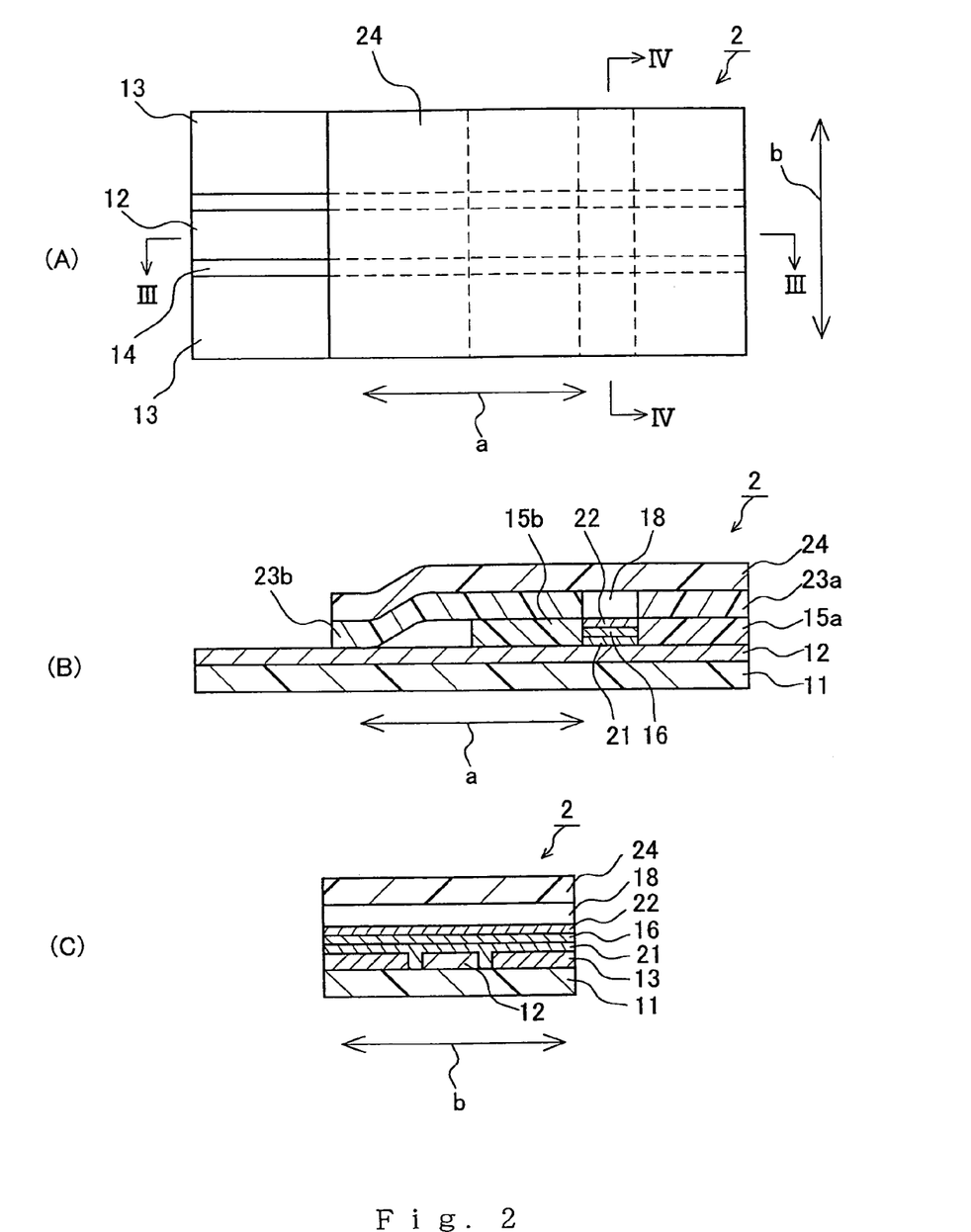
FIG. 2A is a plan view of the biosensor.
FIGS. 2B and 2C are cross-sectional views of the same.

FIGS. 2A–2C show another example of a biosensor of the present invention. FIG. 2A is a plan view of the biosensor, FIG. 2B is a cross-sectional view taken along the line III—III of FIG. 2A, and FIG. 2C is a cross-sectional view taken along the line IV—IV of FIG. 2A. In FIGS. 2A–2C, the same components as those in FIGS. 1A–1C bear the same reference numeral.

As shown in the drawings, in this biosensor 2, an electrode system including a working electrode 12 and counter electrodes 13 is disposed on a substrate 11. A laminate, in which an inorganic gel-containing layer 21, a reagent layer 16, and a surfactant-containing layer 22 are laminated in this order, is formed on one end portion (at the upper right of FIGS. 2A and 2B) of the electrode system. The reagent layer 16 contains a reagent and particulates. The two counter electrodes 13 are disposed on the opposite ends in the width direction (the direction indicated by the arrow "b") of the substrate 11, and the working electrode 12 is disposed in the center in the width direction of the substrate 11. These electrodes 12 and 13 extend in the longitudinal direction (the direction indicated by the arrow "a") of the substrate 11. An insulating portion 14 is formed between the working electrode 12 and each of the counter electrodes 13. On the end portion of the electrode system, first spacers 15a and 15b are disposed so as to be perpendicular to the electrode system. The laminate including the inorganic gel-containing layer 21, reagent layer 16, and surfactant-containing layer 22 is disposed between the first spacers 15a and 15b. On the first spacers 15a and 15b, second spacers 23a and 23b further are disposed. A cover 24 is disposed on the second spacers 23a and 23b so as to cover the upper portion of the laminate, thereby forming a hole passing through the biosensor in the width direction between the cover 24 and the laminate. This hole serves as a sample supply hole 18. This biosensor 2 has the same configuration as that of the biosensor according to Embodiment 1 unless otherwise stated.

The content of the inorganic gel in the inorganic gel-containing layer 21 can be determined as appropriate, depending on the type or the amount of the sample to be supplied, the type of the inorganic gel, or the like. For example, the content of the inorganic gel for about 2 μL of a sample can be in a range from 0.1 to 1000 μg, and preferably 0.5 to 500 μg.

The content of the surfactant in the surfactant-containing layer 22 can be determined as appropriate, depending on the type or the amount of the sample to be supplied, the type of the surfactant, or the like. For example, the content of the surfactant for about 2 μL of a sample can be in a range from 0.01 to 100 μg, and preferably 0.05 to 50 μg.

The biosensor 2 in which the inorganic gel-containing layer 21, the reagent layer 16, and the surfactant-containing layer 22 are laminated can be produced, for example, in the following manner. Unless otherwise stated, the biosensor 2 can be produced in the same manner as that in Embodiment 1.

The first spacers 15a and 15b are disposed on the substrate 11 on which the electrodes have been disposed. A solution containing an inorganic gel is prepared, and then, the solution is poured into the space between the spacers 15a and 15b and dried. Subsequently, a solution containing a reagent and particulates and a solution containing a surfactant are poured and dried, respectively, in the same manner as described above. Thus, the inorganic gel-containing layer 21, the reagent layer 16, and the surfactant-containing layer 22 are laminated in this order. Thereafter, the second spacers 23a and 23b further are disposed on the first spacers 15a and 15b, and the cover 24 is disposed on the second spacers 23a and 23b so as to cover the top face of the surfactant-containing layer 22. As a result, a hole serving as the sample supply hole 18 is formed between the cover 24 and the surfactant-containing layer 22.

By forming the second spacers as described above, it becomes possible to adjust the height of the hole 18. The second spacers may be formed of the same material as that of the first spacers, and can be produced in the same manner as that for producing the first spacers.

The solution containing the inorganic gel preferably is stirred for 1 hour or more, more preferably 5 hours or more, to prevent the inorganic gel from settling. For the same reason, it is preferable to continue stirring during use. There is no limitation regarding the concentration of the inorganic gel in the solution, but the concentration of the inorganic gel can be in a range from 0.01 to 10 wt %, for example, and preferably 0.05 to 5 wt %.

(Embodiment 3)

Figure 3:
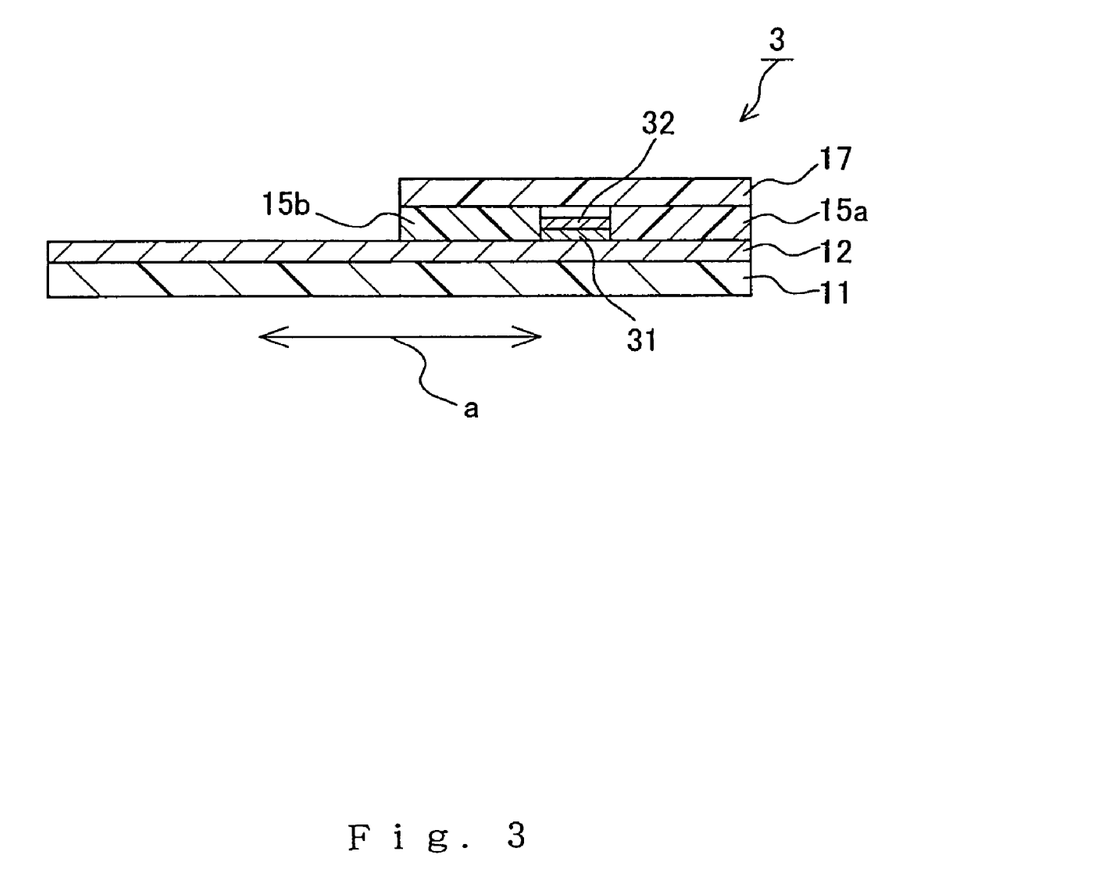
FIG. 3 is a cross-sectional view showing still another example of a biosensor of the present invention.

This embodiment is an example of the biosensor of the present invention in which a reagent layer is a laminate including a reagent-containing layer and a particulate-containing layer. FIG. 3 is a cross-sectional view of this biosensor. In FIG. 3, the same components as those in FIGS. 1A–1C bear the same reference numeral.

As shown in FIG. 3, the biosensor 3 has the same configuration as in Embodiment 1, except that a particulate-containing layer 32 is laminated on the substrate 11, on which the electrodes have been disposed, via a reagent-containing layer 31. The reagent-containing layer 31 and the particulate-containing layer 32 can be formed in the following manner, for example. First, a solution containing a reagent and a solution containing particulates are prepared. The solution containing the reagent is poured into the space between the spacers and dried, and thereafter, the solution containing the particulates is poured thereon and dried.

In this biosensor 3, as in the case of the biosensor of Embodiment 2, an inorganic gel-containing layer may be formed on the electrodes separately before forming a reagent layer (in the present embodiment, the reagent-containing layer and the particulate-containing layer), and then, the reagent-containing layer and the like may be formed on this inorganic gel-containing layer. Also, a surfactant-containing layer further may be laminated on the particulate-containing layer.

It is to be noted that a biosensor of the present invention is not limited to the embodiments described above. For example, all of the layers included in the biosensor may contain particulates and/or inorganic gel. Also, all of the layers may contain both of them.

EXAMPLES

Hereinafter, examples of the present invention will be described along with a comparative example.

Example 1

A biosensor provided with gold electrodes (hereinafter, referred to as "gold electrode biosensor") as shown in FIGS. 2A–2C was produced in the following manner. First, a transparent PET sheet having a length of 30 cm, a width of 30 cm, and a thickness of 250 μm (hereinafter the same) was prepared as a supporting member, and gold was deposited on one surface of the PET sheet. The deposition of the gold was performed under the same conditions as described above. The purity of the gold was 99.95% or higher.

Then, using a kisscut device, linear slits having a depth of 0.1 mm and a width of 0.1 mm were formed on the surface on which the gold was deposited of the PET sheet. The slits were formed in one direction so that the distance between the adjacent two slits would be 1 mm and 5 mm alternately (hereinafter, referred to as "half cut"). These slits served as insulating portions 14, thereby dividing the gold deposited into a working electrode 12 and counter electrodes 13. In the end, the PET sheet would be cut into several pieces to produce biosensors. Thus, the width of the working electrode 12 would be 1 mm, the width of the counter electrodes 13 would be 2.5 mm, and the width of the insulating portions 14 would be 0.1 mm.

The PET sheet was cut to separate a piece having a length of 20 mm and a width of 170 mm using a cutting machine (Kinematic Automation, Inc.; product name Matrix 2360). The PET sheet thus cut out was then subjected to a treatment for hydrophilicity so as to make the surface on which the gold was deposited hydrophilic. The treatment was performed in the following manner. First, the sheet was immersed in a 10 mmol/L 2-mercaptoethanol solution (solvent: ethanol) for 30 minutes, and was washed with ethanol and then with purified water. After that, the sheet was dried at room temperature in a clean bench.

Subsequently, two single-faced polyamide tapes (Sumitomo 3M Limited; product name Y-5579; 42 μm thickness) as first spacers 15a and 15b were attached to predetermined positions of the surface on which the gold was deposited. The spacers 15a and 15b were apart from each other by a distance of 1 mm. The spacers 15a and 15b had a length of 5 mm and a width of 170 mm.

Next, an inorganic gel-containing layer 21 was formed in the space between the spacers 15a and 15b. First, 150 mg of an inorganic gel (CO-OP CHEMICAL Co. Ltd.; product name Lucentite SWN) and 50.0 g of purified water were poured into a siliconized wide mouthed bottle, and stirred at room temperature overnight (10 hours or longer at 500 rpm). Thus, a solution for forming the inorganic gel-containing layer 21 (hereinafter, this solution is referred to as "solution A") was prepared. In order to prevent the inorganic gel from settling, the solution A was prepared immediately before use, and stirring was continued when the solution A was dispensed as described later.

The solution A was dispensed into the space between the first spacers 15a and 15b on the PET sheet using a syringe. The amount of the solution A to be dispensed was set to 1.74 µL for the area of 6 mm×1 mm (corresponding to one biosensor) of the surface onto which the solution A was to be dispensed. After the dispensation, the PET sheet was placed in a clean bench or a desiccator and allowed to stand still for 30 minutes or longer at room temperature so that the solution A was dried. The PET sheet further was dried using a dryer in an atmosphere of 35° C. and a relative humidity of 10% or lower for 30 minute (hereinafter, such drying is referred to as "honey drying"), thus forming the inorganic gel-containing layer 21.

Subsequently, a reagent layer 16, which was a single layer containing particulates, an inorganic gel, and a reagent, was formed on the inorganic gel-containing layer 21. First, a solution for forming the reagent layer 16 (hereinafter, this solution is referred to as "solution B") was prepared in the following manner. 400 mg of an inorganic gel (the above-described Lucentite SWN) and 50.0 g of purified water were poured into a siliconized wide mouthed bottle, and stirred at room temperature (10 hours or longer at 500 rpm). Then, 1.0 mL of the inorganic gel solution, 3.0 mL of purified water, and 320 mg of potassium ferricyanide (Nacalai Tesque, Inc.) were poured into a brown bottle, and stirred at room temperature so that the potassium ferricyanide was dissolved completely. Thus, a potassium ferricyanide solution was prepared. Next, 2.40 KU of glucose oxidase (Amano Pharmaceutical Co., Ltd) and 500 mg of particulates (SEKISUI PLASTICS Co., Ltd.; product name BMX-5; an average particle diameter 5 µm; a raw material compound PMMA) were poured into another brown bottle, and 2.0 mL of the potassium ferricyanide solution further was added thereto. The mixture was stirred sufficiently until they were mixed uniformly. The solution obtained was used as the solution B. During stirring, extreme care was taken not to generate air bubbles in the solution. Furthermore, in order to prevent the particulates from settling, the solution B was dispensed as described later while being stirred.

The solution B was dispensed onto the surface of the inorganic gel-containing layer 21 on the PET sheet using a dispenser (Bio•dot Ltd.; product name Dispenser System). The amount of the solution B to be dispensed was set to 1.30 µL for the area of 6 mm×1 mm (corresponding to one biosensor) of the surface onto which the solution B was to be dispensed. After the dispensation, the sheet was placed in an oven and dried at 50° C. for 10 minutes under non ventilating conditions. Thereafter, the honey drying was performed in the same manner as above for 10 minutes, thus forming the reagent layer 16.

Next, a surfactant-containing layer 22 was formed on the reagent layer 16. First, 250 mg of high purity egg yolk lecithin (Q. P. Corporation) and 50.0 mL of ethanol were poured into a brown bottle, and stirred at room temperature until they were mixed uniformly. Thus, a solution for forming the surfactant-containing layer 22 (hereinafter, this solution is referred to as "solution C") was prepared.

The solution C was dispensed onto the surface of the reagent layer 16 on the sheet 11 using the above-described dispenser. The amount of the solution C to be dispensed was set to 0.30 µL for the area of 6 mm×1 mm (corresponding to one biosensor) of the surface onto which the solution C was to be dispensed. After the dispensation, the sheet 11 was subjected to the honey drying (drying time: 15 minutes), thus forming the surfactant-containing layer 22. Then, the sheet 11 was placed in a reduced-pressure container together with a molecular sieve, and subjected to reduced-pressure drying overnight under the conditions of room temperature and a pressure of about 100 Pa.

Next, as second spacers, double-faced tapes having a PET film as a core material (DAINIPPON INK AND CHEMICALS, INCORPORATED; product name Didac double-faced adhesive tape; 150 µm thickness) were disposed on the first spacers 15a and 15b. The second spacer 23a had a length of 5 mm and a width of 160 mm, and the second spacer 23b had a length of 5 mm and a width of 160 mm. Further, a film made of PET having a length of 15 mm, a width of 160 mm, and a thickness of 188 µm was attached so as to cover the second spacers 23a and 23b and the space therebetween. This film served as a cover 24.

Then, using the above-described cutting machine, the thus obtained laminate was cut so as to have a width of 6 mm. As a result, a desired biosensor having a length of 20 mm and a width of 6 mm was obtained. The biosensor was stored in a brown bottle together with 3 g or more of a molecular sieve until time of use.

Example 2

A biosensor was produced in the same manner as in Example 1, except that the solution B was prepared using, as an inorganic gel, a product named Laponite XLS (Laporte Industries, Limited) in place of the Lucentite SWN.

Example 3

A biosensor was produced in the same manner as in Example 1, except that the solution B was prepared using 1.0 mL of purified water in place of 1.0 mL of the inorganic gel solution.

Example 4

A biosensor was produced in the same manner as in Example 1, except that the solution A was prepared using, as an inorganic gel, the Laponite XLS in place of the Lucentite SWN and that the solution B was prepared using 1.0 mL of purified water in place of 1.0 mL of the inorganic gel solution.

Example 5

A biosensor provided with carbon electrodes (hereinafter, referred to as "carbon electrode biosensor") as shown in FIGS. 2A–2C was produced in the following manner. Unless otherwise stated, the biosensor was produced in the same manner as in Example 1.

On one surface of the transparent PET sheet as a substrate 11, a working electrode 12 and counter electrode 13 were formed by printing carbon ink thereon. The printing was performed using a screen printing machine under the following conditions: SUS 300 mesh; a squeegee pressure of 3 to 5 MPa, a printing speed of 0.5 m/s, a coating speed of 0.5 m/s, a clearance of 2.0 mm; and an off contact of 15°. The sheet was dried at 90° C. for 30 minutes.

Next, a resist ink containing an insulating UV curing resin as a main component was printed on the electrode side surface of the PET sheet by resist printing. The resist ink was then dried, thus forming first spacers 15a and 15b. The resist printing was performed using a screen printing machine under the following conditions: polyester 300 mesh screen;

a squeegee pressure of 3 to 5 MPa, a printing speed of 0.15 m/s, and a coating speed of 0.15 m/s, a clearance of 4.0 mm; and an off contact of 15°. The size and the like of the first spacers 15a and 15b were set to be the same as those in Example 1, and the thickness thereof was adjusted so as to be 10 µm after the drying process as described later. The above-described drying was performed under the condition of 3.7 m/s using an UV dryer.

Next, an inorganic gel-containing layer 21 was formed in the space between the spacers 15a and 15b. The solution A was prepared using, as an inorganic gel, 150 mg of the Laponite XLS in place of the Lucentite SWN. The amount of the solution A to be dispensed was set to 1.45 µL for the area of 6 mm×1 mm (corresponding to one biosensor) of the surface onto which the solution A was to be dispensed.

Subsequently, a reagent layer 16 was formed on the inorganic gel-containing layer 21. A solution B for forming the reagent layer 16 was prepared in the following manner. 3.0 mL of purified water, 750 mg of the particulates, and 240 mg of potassium ferricyanide were poured into a brown bottle, and stirred so that the potassium ferricyanide was dissolved completely. Thus, a potassium ferricyanide solution was prepared. Subsequently, 2.40 KU of glucose oxidase and 2.0 mL of the potassium ferricyanide solution were poured into another brown bottle, and the mixture solution was stirred sufficiently until they were mixed uniformly. The solution obtained was used as the solution B. The amount of the solution B to be dispensed was set to 1.08 µL for the area of 6 mm×1 mm (corresponding to one biosensor) of the surface onto which the solution B was to be dispensed.

After that, a surfactant-containing layer 22 was formed, second spacers 23a and 23b and a cover 24 were deposited to form a laminate, and the laminate was cut to obtain a desired biosensor, in the same manner as in Example 1.

Example 6

A biosensor was produced in the same manner as in Example 5, except that the inorganic gel-containing layer 21 was not formed.

Comparative Example 1

A conventional biosensor was produced in the following manner. First, carbon electrodes were formed on the PET sheet in the same manner as in Example 5. Further, spacers were formed in the same manner as in Example 1. A 3 wt % aqueous solution of carboxymethyl cellulose (CMC) was prepared, and the CMC solution was then dispensed onto the electrode system on the PET sheet and dried to form a CMC layer. The amount of the CMC solution to be dispensed was set to 3 µL for the area of 6 mm×1 mm (corresponding to one biosensor) of the surface onto which the CMC solution was to be dispensed. Next, 320 mg of potassium ferricyanide was added to 4.0 mL of purified water. The mixture was stirred so that the potassium ferricyanide was dissolved completely to prepare a potassium ferricyanide solution. Subsequently, 2.40 KU of glucose oxidase was added to 2 mL of the potassium ferricyanide solution, and the mixture solution was stirred sufficiently until they were mixed uniformly. The reagent solution obtained was dispensed onto the CMC layer, and was dried in the same manner as in Example 1. Thus, a reagent layer was formed. The amount of the reagent solution to be dispensed was set to 1.30 µL for the area of 6 mm×1 mm (corresponding to one biosensor) of the surface onto which the reagent solution was to be dispensed. Thereafter, second spacers were disposed and a cover was attached in the same manner as in Example 1.

With regard to the biosensors of the respective Examples and Comparative Example 1 obtained in the above-described manners, various tests as described below were conducted.

(Influence of Hct on Gold Electrode Biosensor)

With regard to the biosensors of Examples 1 to 4 and Comparative Example, the current value was measured. For the biosensors of Examples 1 to 4, a physiological salt solution (hereinafter, referred to as "Sal"), a physiological salt solution containing glucose (concentration: 1000 mg/L) (hereinafter, referred to as "GSal"), human whole blood (hereinafter, referred to as "WB"), and human blood plasma (hereinafter, referred to as "P") were used as a sample. On the other hand, for the biosensor of Comparative Example, the human whole blood (WB) and the human blood plasma (P) were used as a sample. The Hct value of the human whole blood (WB) was 46%. The glucose concentration in blood plasma was 1270 mg/L in the human whole blood (WB) and the human blood plasma (P).

First, each biosensor was connected to a potentiostat (BAS Co. Ltd.; product name CV 100 W). After the sample was drawn in the biosensor at room temperature, the circuit was held open for 25 seconds. Then, the current value was measured at the time when a voltage was applied for 5 seconds. The voltage applied to the biosensors of Examples 1 to 4 was set to 250 mV, and the voltage applied to the biosensor of Comparative Example was set to 500 mV. The measurement of the current value was carried out three times with regard to the respective biosensors using the respective samples under the same conditions, and the average value was calculated. Further, divergence ratios A and B (%) of the biosensors were obtained using the following Equations (1) and (2), respectively. In these Equations, $E_{Sal}$, $E_{GSal}$, $E_{WB}$, and $E_P$ denote average values of the current values obtained through the measurement using the respective samples. The divergence ratios A and B are values indicating the degree of the influence of impurities in the samples. More specifically, the divergence ratio A is the value mainly relating to the influence of the blood cells, and the divergence ratio B is the value relating to the influence of salts in addition to the influence of the blood cells. As the absolute values of these ratios are smaller, the influence of the impurities is considered to be smaller.

$$\text{Divergence ratio } A\ (\%) = [(E_{WB} - E_P)/E_P] \times 100 \quad (1)$$

$$\text{Divergence ratio } B\ (\%) = [(E_{WB} - E_P)/(E_P - E_{Sal})] \times 100 \quad (2)$$

The average value of the current values and the divergence ratios A and B (%) calculated from the average value using the Equation (1) and (2) are shown in Table 1 below.

TABLE 1

|  | Example 1 | Example 2 | Example 3 | Example 4 | Comparative Example |
|---|---|---|---|---|---|
| $E_{Sal}$ | 0.509 | 0.493 | 0.293 | 0.231 | — |
| $E_{GSal}$ | 2.125 | 2.285 | 1.808 | 2.173 | — |
| $E_{WB}$ | 2.868 | 2.539 | 2.123 | 2.059 | 2.364 |
| $E_P$ | 2.860 | 2.736 | 2.395 | 2.153 | 2.844 |
| Divergence ratio A (%) | 0.3 | −7.2 | −11.3 | −4.4 | −16.9 |
| Divergence ratio B (%) | 0.3 | −8.8 | −12.9 | −4.9 | — |

As shown in Table 1, the absolute value of the divergence ratio A in the biosensors of Examples was smaller than that in the biosensor of Comparative Example. The absolute value of the divergence ratio B in the biosensors of Examples was substantially the same as that of the divergence ratio A. These results demonstrate that the biosensors of Examples are less susceptible to the influence of Hct and can measure the components in blood accurately.

(Examination on Influence of Open Circuit Period)

Using the gold electrode biosensor of Example 4, the current value was measured to examine the influence of a time period for which the circuit is held open (hereinafter, referred to as an "open circuit period"). A physiological salt solution containing glucose (concentration: 5000 mg/L) was used as a sample.

Figure 4:
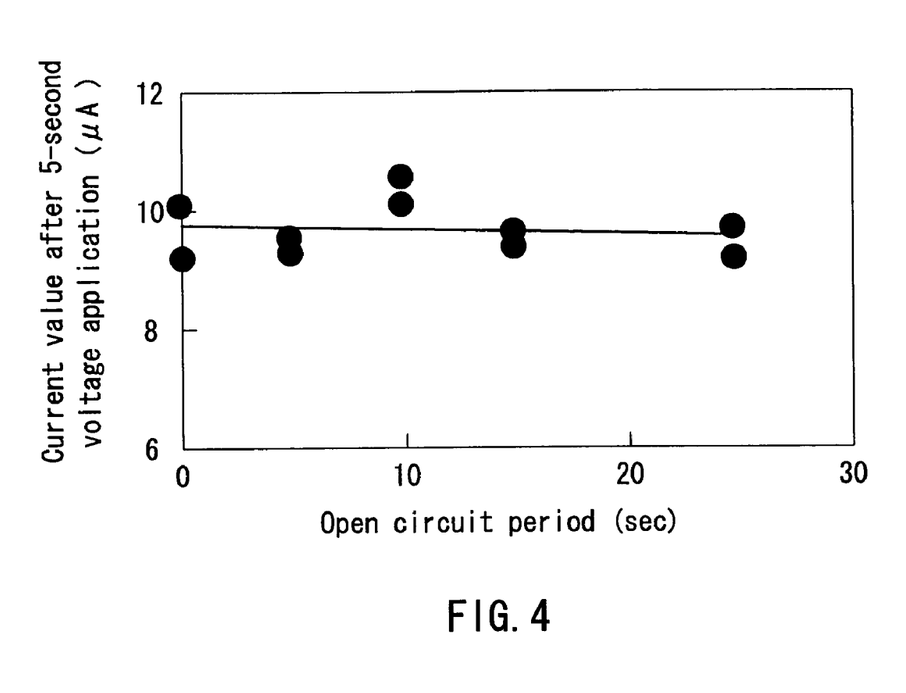
FIG. 4 is a graph showing the correlation between a current value and a time period for which a circuit is held open in one example of the present invention.

First, the biosensor of Example 4 was connected to the potentiostat. After the sample was drawn in the biosensor, the circuit was held open for a predetermined period of time (0, 5, 10, 15, and 25 seconds). Then, the current value was measured at the time when a voltage of 250 mV was applied for 5 seconds. The results are shown in FIG. 4. FIG. 4 is a graph showing the correlation between the open circuit period and the current value.

As shown in FIG. 4, the current value was almost unaffected by the open circuit period. This means that the enzyme reaction proceeded rapidly within a short time after the sample was drawn in the biosensor of Example 4. Accordingly, it can be said that a biosensor of the present invention can measure an analyte rapidly and has an excellent operability.

(Examination on Influence of Hct on Carbon Electrode Biosensor)

With regard to the carbon electrode biosensor of Example 5, the gold electrode biosensor of Example 4, and the biosensor of Comparative Example, the current value was measured. For the biosensors of Examples 4 and 5, a physiological salt solution (Sal), human whole blood (WB), and human blood plasma (P) were used as a sample. On the other hand, for the biosensor of Comparative Example, the human whole blood (WB) and the human blood plasma (P) were used as a sample. The Hct value of the human whole blood (WB) was 49%. The glucose concentration in blood plasma was 1110 mg/L in the human whole blood (WB) and the human blood plasma (P).

First, the gold electrode biosensor of Example 4 and the carbon electrode biosensor of Example 5 were connected to potentiostats, respectively. After the sample was drawn in the biosensors, the current value was measured at the time when a voltage was applied for 20 seconds. The voltage applied to the gold electrode biosensor was set to 250 mV, and the voltage applied to the carbon electrode biosensor was set to 350 mV. On the other hand, the biosensor of Comparative Example was connected to a potentiostat. After the above sample was drawn in the biosensor, the circuit was held open for 25 seconds. Then, the current value was measured at the time when a voltage was applied for 5 seconds. The measurement of the current value was carried out four times with regard to the respective biosensors under the same conditions, and the average value was calculated. Further, divergence ratios A and B (%) were obtained in the same manner as described above.

The average value of the current values and the divergence ratios A and B (%) are shown in Table 2 below.

TABLE 2

|  | Example 5 | Example 6 | Comparative Example |
| --- | --- | --- | --- |
| $E_{Sal}$ | 0.073 | 0.108 | — |
| $E_{WB}$ | 0.757 | 1.075 | 2.206 |
| $E_P$ | 0.766 | 1.140 | 2.404 |
| Divergence ratio A (%) | −1.0 | −6.0 | −8.2 |
| Divergence ratio B (%) | −1.2 | −6.2 | — |

As shown in Table 2, the absolute value of the divergence ratio A in the biosensors of both Examples was smaller than that in the biosensor according to Comparative Example. Also, the absolute value of the divergence ratio B in the biosensors of both Examples was substantially the same as that of the divergence ratio A. These results demonstrate that the biosensors of Examples are less susceptible to the influence of Hct and can measure the components in blood accurately. Also, it is understood from the results that, while the gold electrode biosensor of Example 4 is more effective than the conventional biosensor in avoiding the influence of Hct, the carbon electrode biosensor of Example 5 is still more effective than the gold biosensor of Example 4.

(Influence of Humidity)

With regard to the gold electrode biosensor of Example 4, the carbon electrode biosensors of Examples 5 and 6, and the biosensor of Comparative Example, the current value was measured in the following manner to examine the influence of humidity.

First, the current value was measured with sufficiently-dried unused biosensors. As a sample, a physiological salt solution (Sal) and a physiological salt solution containing glucose (concentration: 100 mg/L) (GSal) were used. Each biosensor was connected to a potentiostat. After the sample was drawn in the biosensor, the circuit was held open for 25 seconds. Then, the current value was measured at the time when a voltage was applied for 5 seconds. The voltage applied to the gold electrode biosensor of Example 4 was set to 250 mV, the voltage applied to the carbon electrode biosensors of Examples 5 and 6 was set to 350 mV, and the voltage applied to the biosensor of Comparative Example was set to 500 mV The measurement of the current value was carried out twice with regard to the respective biosensors under the same conditions, and the average value was calculated. On the other hand, sufficiently-dried unused biosensors were left in a sealed container (Advantec Corp.; product name AE-215) maintained at 40° C. and a relative humidity of 85% for 30 minutes. After that, the current value was measured twice using these biosensors under the same conditions as described above, and the average value was calculated.

The average values of the current values in the biosensors that had not been left in the container were represented by $^1E_{Sal}$ and $^1E_{GSal}$, while those in the biosensors that had left in the container were represented by $^2E_{Sal}$ and $^2E_{GSal}$. Further, the ratios $R_{Sal}$ and $R_{GSal}$ (%) of the average values of the biosensors that had been left in the container to the average values of the biosensors that had not been left in the container were obtained using the following Equations (3) and (4), respectively. As the values of $R_{Sal}$ (%) and $R_{GSal}$ (%) are closer to 100, the influence of humidity is considered to be smaller. The measured values of the respective biosensors are shown in Table 3 below.

$$R_{Sal}(\%) = (^2E_{Sal}/^1E_{Sal}) \times 100 \tag{3}$$

$$R_{GSal}(\%) = (^2E_{GSal}/^1E_{GSal}) \times 100 \tag{4}$$

TABLE 3

|  | Example 4 | Example 5 | Example 6 | Comparative Example |
|---|---|---|---|---|
| $^1E_{Sal}$ | 0.256 | 0.212 | 0.161 | 0.165 |
| $^2E_{Sal}$ | 0.552 | 0.283 | 0.315 | 4.144 |
| $R_{Sal}$ (%) | 216 | 133 | 196 | 2519 |
| $^1E_{GSal}$ | 2.191 | 1.614 | 1.499 | 2.498 |
| $^2E_{GSal}$ | 2.357 | 1.711 | 1.963 | 6.164 |
| $R_{GSal}$ (%) | 108 | 106 | 131 | 247 |

As shown in Table 3, the values of $R_{Sal}$ (%) and $R_{GSal}$ (%) in the biosensor of Examples were closer to 100 than those in the biosensor of Comparative Example, which means the influence of humidity was smaller. Therefore, it is understood that a biosensor of the present invention is not susceptible to the influence of humidity.

INDUSTRIAL APPLICABILITY

As specifically described above, a biosensor of the present invention is not susceptible to the influence of a substance other than an analyte, such as solid components, soluble components, and insoluble components, contained in a sample or the influence of humidity. Therefore, the analyte can be measured with high precision. In addition, the biosensor is superior in terms of operability because an enzyme reaction proceeds rapidly.

What is claimed is:

1. A biosensor comprising a substrate, a reagent layer containing a reagent, and an electrode system including a working electrode and a counter electrode, the electrode system being disposed on the substrate, and the reagent layer being formed on the electrode system,
    wherein the reagent layer further comprises particulates, and
    an inorganic gel-containing layer containing an inorganic gel is formed between the electrode system and the reagent layer.

2. The biosensor according to claim 1, wherein the reagent layer is a single layer.

3. The biosensor according to claim 1, wherein the reagent layer is a laminate comprising a reagent-containing layer containing the reagent and a particulate-containing layer containing the particulates.

4. The biosensor according to claim 3, wherein the particulate-containing layer is formed on the electrode system via the reagent-containing layer.

5. The biosensor according to claim 1, wherein the reagent layer further comprises an inorganic gel.

6. The biosensor according to claim 5, wherein the inorganic gel is a gel of clay mineral.

7. The biosensor according to claim 6, wherein the clay mineral is expansive phyllosilicate.

8. The biosensor according to claim 1, wherein a surfactant-containing layer containing a surfactant further is formed on the reagent layer.

9. The biosensor according to claim 1, wherein an average particle diameter of the particulates is in a range from 0.1 to 45 µm.

10. The biosensor according to claim 1, wherein particle size distribution of the particulates is in a range from 0.01 to 100 µm.

11. The biosensor according to claim 1, wherein the particulates are spherical.

12. The biosensor according to claim 1, wherein the particulates are formed of a polymer compound.

13. The biosensor according to claim 12, wherein the polymer compound does not contain an impurity causing electrolysis and is electrochemically inactive.

14. The biosensor according to claim 12, wherein the polymer compound is water-insoluble.

15. The biosensor according to claim 12, wherein the polymer compound is a polymer or a copolymer containing at least one of acrylic acid, methacrylate, maleate, acrylic ester, methacrylic acid ester, maleate ester, and styrene derivative monomer, or a polyamide-based polymer compound.

16. The biosensor according to claim 1, wherein the electrodes are at least one selected from the group consisting of gold electrodes, carbon electrodes, and silver electrodes.

17. The biosensor according to claim 1, wherein the reagent contains a redox enzyme.

18. The biosensor according to claim 1, wherein the reagent contains a redox enzyme and an electron acceptor in a reaction of the enzyme.

19. The biosensor according to claim 1, wherein a sample to be measured is blood.

* * * * *